United States Patent [19]

Badamchian

[11] Patent Number: 5,132,401

[45] Date of Patent: Jul. 21, 1992

[54] MB-35 A PEPTIDE ENHANCING THE PRODUCTION OF GROWTH HORMONE AND PROLACTIN FROM THE ANTERIOR PITUITARY

[75] Inventor: Mahnaz Badamchian, Rockville, Md.

[73] Assignee: George Washington University, Office of Sponsored Research, Washington, D.C.

[21] Appl. No.: 409,434

[22] Filed: Sep. 19, 1989

[51] Int. Cl.$^5$ .......................... C07K 7/10; C07K 7/48; C07K 13/00; A61K 37/43

[52] U.S. Cl. .................................. 530/324; 530/300; 530/301; 530/837

[58] Field of Search ............... 530/301, 324, 326, 399, 530/837; 514/12

[56] References Cited

U.S. PATENT DOCUMENTS

| | | | |
|---|---|---|---|
| 4,061,737 | 12/1977 | Alburn et al. | 424/177 |
| 4,150,147 | 4/1979 | Lien | 424/330 |
| 4,410,513 | 10/1983 | Momany | 424/177 |
| 4,411,890 | 10/1983 | Momany | 424/177 |
| 4,617,149 | 10/1986 | DiMarchi et al. | 530/324 |
| 4,622,312 | 11/1986 | Felix et al. | 514/12 |
| 4,649,131 | 3/1987 | Felix et al. | 514/12 |
| 4,728,609 | 3/1988 | Bhatt et al. | 435/68 |
| 4,732,972 | 3/1988 | Felix et al. | 530/324 |
| 4,734,399 | 3/1988 | Felix et al. | 514/12 |
| 5,070,076 | 12/1991 | Morozov et al. | 530/387 |

FOREIGN PATENT DOCUMENTS

1188221 6/1985 Canada.
J641698 3/1985 Japan.

OTHER PUBLICATIONS

Reichhart et al., The Primary Structure of Two Polypeptide Chains from preparations of homeostatic thymus hormone (HTHα and HTHβ), *FEBS Letters* vol. 188(1) Aug. 1988, pp. 63-67.

Schulz & Schirmer, *Principles of Protein Structure*, 1979, pp. 14-16.

Thomas Creighton, *Proteins*, 1984 pp. 37, 159.

Geoffrey Zubay, *Biochemistry*, 1988, p. 1047.

Sato et al., CA88(23):164579p 1978.

Spangelo, et al., "Thymosin Fraction 5 Stimulates Prolactin and Growth Hormone Release from Anterior Pituitary Cells in Vitro", *Endocrinology*, vol. 121, No. 6, pp. 2035-2043 (1987).

Spangelo, et al., "Stimulation of in vivo antibody production and concanavalin-A-induced mouse spleen cell mitogenesis by prolactin", *Immunopharmocology*, 14 (1987) pp. 11-20.

Reichhart, et al., "Preparations of homeostatic thymus hormone consist predominantly of histones 2A and 2B and suggest additional histone functions", *Proc. Natl. Acad. Sci. USA*, vol. 82, pp. 4871-4875, Aug. 1985.

*Primary Examiner*—Robert A. Wax
*Assistant Examiner*—Stephen Walsh
*Attorney, Agent, or Firm*—Sherman & Shalloway

[57] ABSTRACT

A peptide of the formula

Ala—Ile—Arg—Asn—Asp—Glu—Glu—Leu—Asn—Lys—

Leu—Leu—Gly—Lys—Val—Thr—Ile—Ala—Gln—Gly—

Gly—Val—Leu—Pro—Asn—Ile—Gln—Ala—Val—Leu—

Leu—Pro—Lys—Lys—Thr has been isolated from thymosin fraction 5 (TF-5) and synthetically produced. This peptide, which has 100% homology with a region of histone 2A is able to stimulate and enhance the production of growth hormone (GH) and prolactin (PRL) by anterior pituitary cells. The peptide can be used alone or in combination with another growth hormone stimulant, such as growth hormone releasing factor (GRF), or prolactin hormone stimulant, such as thyrotropin releasing hormone (TRH) to increase the production of GH and PRL beyond that achievable with GRF and TRH alone.

2 Claims, 7 Drawing Sheets $* = p < 0.05$

\* = p < 0.01
\*\* = p < 0.05

\* = p < 0.05

9.3
pI
3.5
1 2 3 4

92K
66K
45K
31K
21K
14K 3756
1 2

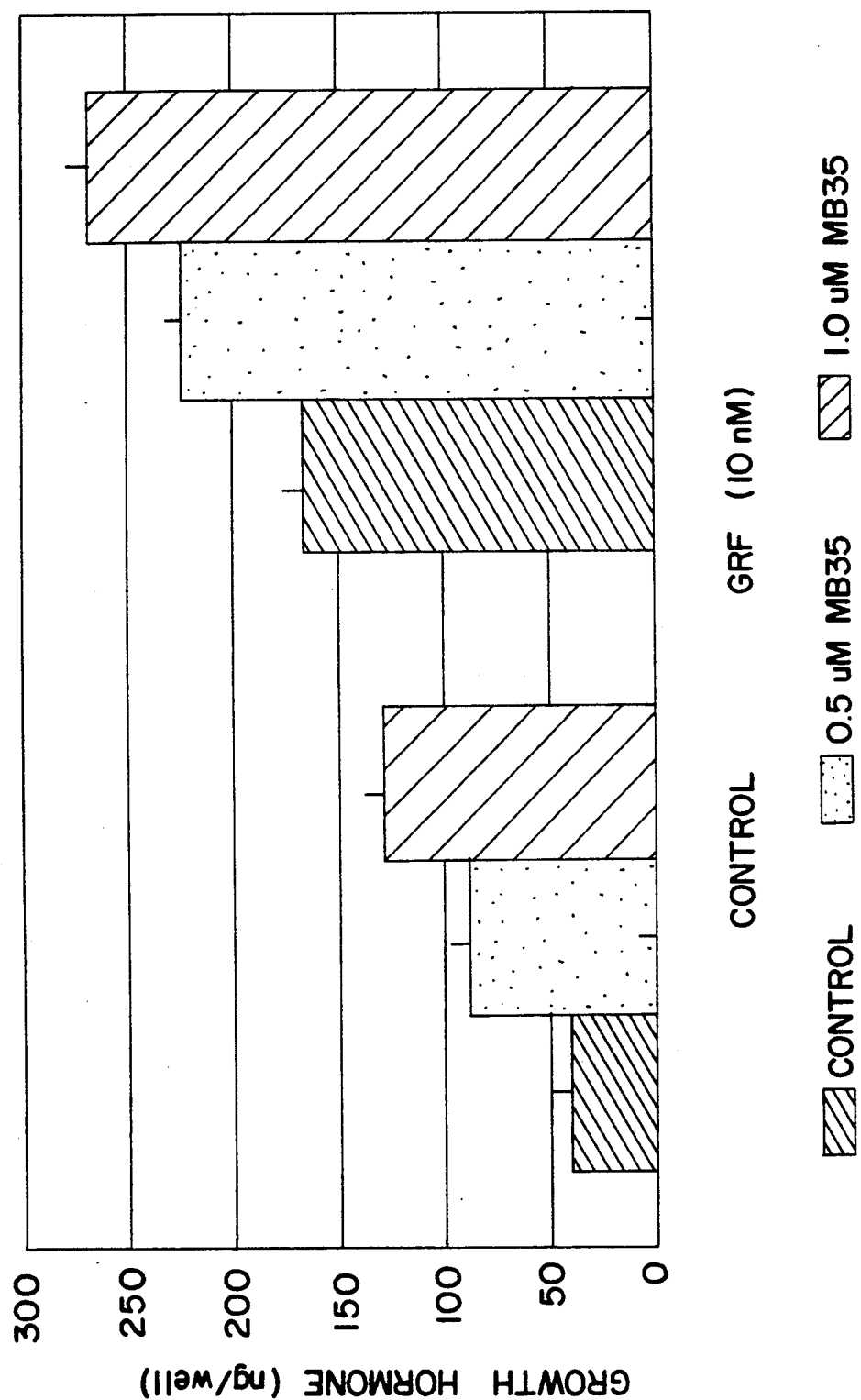

MB-35 A PEPTIDE ENHANCING THE PRODUCTION OF GROWTH HORMONE AND PROLACTIN FROM THE ANTERIOR PITUITARY

BACKGROUND OF THE INVENTION (1) Field of the Invention

This invention relates to a novel peptide and to the use thereof for stimulating prolactin and growth hormone production.

(2) Discussion of Prior Art

Thymosin fraction 5 (TF-5) is a partially purified thymus gland preparation containing 40 to 60 peptides. TF-5 has been known to possess important immunopotentiating effects in animals and humans and can improve the physiology and function of the thymus gland. It has recently been demonstrated that TF-5 can also modulate neuroendocrine responses at the level of the pituitary gland and can, for example, stimulate production in vitro of prolactin (PRL) and Growth Hormone (GH) from anterior pituitary cells; see Spangelo, et al., Endocrinology, Vol. 121, No. 6, pp. 2035-2043 (1987).

The PRL and GH hormones are straight chain polypeptides produced in the anterior pituitary under the influence of corresponding releasing factors produced by the hypothalamus gland upon appropriate neural input. A primary biological activity of growth hormone (GH) (also known as somatotropin -STH) is the regulation of growth of body, organs and bones. GH also exerts a regulating action on the $\alpha$ cells of the pancreas for the production of the hormone glucagon which in turn acts on the liver to regulate the production of somatomedins. The primary biological activities of PRL that have been extensively studied and documented include the regulation of growth of the mammary gland, lactation and corpus luteum function Most recently it has also been observed that receptors for PRL are found on lymphocytes and that administration of PRL enhances immune responses (c.f. Spangelo, et al., Immunopharmocology, 14 (1987) pp. 11-20).

Growth in animals is believed to be regulated by a cascade of bio-regulatory molecules. Thus, the hypothalamus produces growth hormone releasing factor (GRF) and thyrotropin releasing hormone (TRH) which, in turn, act upon the pituitary to cause release of GH and PRL, respectively. Conversely, the pituitary is maintained under negative feedback by, for example, somatostatin (somatotropin release inhibiting factor - SRIF) and dopamine, to inhibit, respectively, secretion of GH or PRL.

Various clinical symptoms have been associated with deficiencies in the normal production of either of these hormones. For example, growth hormone production abnormalities may result in hypopituitary dwarfism and diabetes. Deficiencies or abnormalities in production of prolactin may result in deficient mammary gland development or inability to induce lactation. Other applications for human treatment by promoting growth hormone levels and/or prolactin include, for example, diffuse gastric bleeding, pseudoarthrosis, burn therapy, wound healing, dystrophy, bone knitting, osteoporosis, especially post-menopausal osteoporosis, and ovarian dysgenesis.

Deficiencies in production of growth hormone have been treated by administration of growth hormone derived from, for example, pituitary glands of human cadavers, or as a genetically engineered product. However, the former technique is inefficient, requiring a scarce source, while the latter is also expensive, and furthermore, yields only a single species of growth hormone, whereas, it has recently been disclosed that in the body a whole family of growth hormone compounds are normally secreted.

Various ways are known to stimulate release of growth hormone in vitro and in vivo. For example, chemicals such as arginine, L-3,4-dihydroxyphenylalanine (L-DOPA), glucagon, vasopressin, indirectly cause growth hormone to be released from the pituitary by acting in some fashion on the hypothalamus. Prostaglandin $E_1$ and $E_2$, theophylline, and certain cyclic nucleotides are believed to act directly on the pituitary to release growth hormone, however, their action is not believed to specifically release growth hormone nor are they believed to act at the growth-hormone-releasing hormone (GRF) receptors in the peripheral membrane and of the pituitary cell to initiate growth hormone release. Other potent GH releasing agents include galanin and epinephrine.

Another level of the regulation of pituitary hormone secretion is feedback control from target tissues, which may be negative or positive in nature. Among the many target tissues with feedback control of prolactin and GH secretion, the thymus has been shown to be one with a positive signal. For instance, neonatal thymectomy of the mouse results in severe degranulation of the acidophilic cells of the anterior pituitary, Bianchi, E., et al., 1971, J. Endocr., 51:1, and reduced serum levels of GH, Michael, S. D., et al., 1980, Biol. Reprod., 22:343. In addition, nude mice have smaller acidophilic cells, which are also degranulated, Ruitenberg, E. G., et al., 1977, J. Path., 121:225. Adult nude mice have reduced prolactin serum levels compared to normal littermates, Pierpaoli, W., et al., 1976, Clin. Exp. Immunol., 24:501. In the event that thymic tissue is implanted into these animals soon after birth, normal serum levels of prolactin will be found in adulthood, see Pierpaoli, id. In utero thymectomy of the Rhesus monkey also results in a 3-fold reduction of prolactin in the blood compared to surgical controls two days after birth, Healy, D. L., et al., 1985, Biol. Reprod., 32:1127.

Other pituitary hormones may also be regulated by the thymus gland. Neonatal thymectomy of the mouse results in reductions of serum luteinizing hormone (LH) and follicle stimulating hormone (FSH) levels, Michael, supra. LH and FSH are reduced in both the pituitary and the blood of the nude mouse, Rebar, R. W., et al., 1981, Endocrinology, 108:120 and Rebar, R. W., et al., 1982, Biol. Reprod., 27:1267. While both sexes had similar reductions in the gonadotropins, only the female nude mouse achieved complete normalization of pituitary hormone levels upon implantation with thymic tissue on the first day of life, Rebar, R. W., et al., 1980, Endocrinology, 107:2130. These hormonal changes may explain the ovarian dysgenesis and reduced ovarian weight often observed in the nude mouse, Ruitenberg, supra, and Shire, J. G. M., et al., 1974, Comp. Biochem, Physiol., 47A:93 and following neonatal thymectomy in normal rodents, Nishizuka, Y., et al., 1969, Science, 166:753.

GRF and analogs thereof have been isolated and synthesized by various techniques, including solid state peptide synthesis and genetic engineering; see, for example, U.S. Pat. Nos. 4,728,609, 4,734,399 and 4,732,972. There have also been proposed various synthetic peptides having pituitary growth hormone releasing activity; see, for example, U.S. Pat. Nos. 4,649,131, 4,622,312, 4,617,149, 4,411,890, 4,410,513 and many others.

Similarly, stimulation of PRL release from the pituitary has been proposed for various natural and synthetic chemicals, including, for example, the narcotic-analgesic morphine, the analgesic peptide methionine-enkephalin, analogs of methionine enkephalin, (-)-13β-amino-5,6,7,8,9,10,11,12-octahydro-5α-methyl-5,11-methanobenzocyclodecene-3-ol, thyrotropin releasing hormone (TRH), and other peptides, such as angiotensin II (AII), and neurotensin (NT); see, for example. U.S. Pat. Nos. 4,061,737 and 4,150,147.

Both PRL and GH are anabolic hormones with regard to their metabolic actions on the thymus, spleen, lymph nodes and other components of the immune system. Abnormalities in pituitary function result in significant alterations in both immune and reproductive endocrine reactions that can be traced to reduced GH and/or PRL production.

BRIEF DESCRIPTION OF THE DRAWINGS

FIG. 13 is a bar graph showing the effect of combinations of MB-35 and GRF in the in vitro assay for GH production;

SUMMARY OF THE INVENTION

Figure 1:
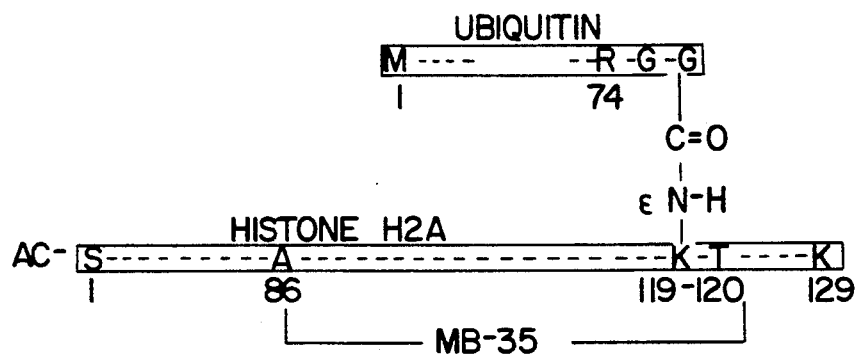
FIG. 1 is a diagrammatic representation of the relationship between the invention peptide (MB-35) and the nuclear protein A24.

The present inventor has now isolated, purified and identified a peptide present in TF-5 which has the ability to regulate pituitary hormone secretion for the production of growth hormone and prolactin. This peptide, which will be referred to hereinafter, for simplicity as MB-35, is a 35 amino acid peptide, which has, quite surprisingly, been found to have 100% homology to the residues 86-120 of the nuclear protein histone H2A isolated from human, chicken, rat and bovine thymus. Histone 2A from calf thymus does not exhibit any biological activity in the PRL and GH assays used to determine the biological activity of MB-35.

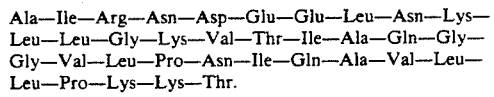

Ala—Ile—Arg—Asn—Asp—Glu—Glu—Leu—Asn—Lys—
Leu—Leu—Gly—Lys—Val—Thr—Ile—Ala—Gln—Gly—
Gly—Val—Leu—Pro—Asn—Ile—Gln—Ala—Val—Leu—
Leu—Pro—Lys—Lys—Thr.

MB-35 has a molecular weight of 3756 and a pI in the range of 9.3 as determined by slab gel isoelectric focusing at a pH range of 3.5-9.5.

MB-35 can be used to stimulate in vitro release of growth hormone and/or prolactin from anterior pituitary cells by incubating the cells in a cell culture medium containing an effective amount of MB-35. MB-35 can also be used in an additive manner to increase the yield of GH and PRL induced by the releasing factors GRF and TRH significantly beyond that observed with the releasing factors alone. Thus, the invention also encompasses the use of one or more additional inducers for production of GH and/or PRL or an inhibitor for either GH or PRL when the production of only one of these pituitary hormones is desired. For example, MB-35 can be used in combination with another inducer for GH, such as GRF, and/or an inhibitor for PRL secretion, such as dopamine. Or, where PRL is the desired hormone, MB-35 can be used in combination with another PRL inducing agent, such as TRH, and/or an inhibitor for GH secretion, such as SRIF. Where high yields of both GH and PRL are desired inducers for both of these hormones can be made present together with MB-35, for example, GRF and TRH.

In a preferred embodiment of the invention, a therapeutically or physiologically effective amount of MB-35 is administered to a human or an animal in need of same to stimulate in vivo production of growth hormone and/or prolactin. Here again, MB-35 may be used in combination with one or more other agents capable of stimulating production of GH, such as GRF, and/or PRL, such as TRH, and/or with an agent capable of inhibiting production of GH or PRL, such as SRIF or dopamine, respectively.

Accordingly, the present invention provides a novel peptide having the ability to stimulate prolactin and growth hormone release from the anterior pituitary cells. The peptides of this invention have from about 20 to 50 amino acids including the whole or part of the peptide having the amino acid sequence represented by the formula (I)

Ala—Ile—Arg—Asn—Asp—Glu—Glu—Leu—Asn—Lys—

Leu—Leu—Gly—Lys—Val—Thr—Ile—Ala—Gln—Gly—

Gly—Val—Leu—Pro—Asn—Ile—Gln—Ala—Val—Leu—

Leu—Pro—Lys—Lys—Thr     (I)

or an analog thereof having part or all of the primary structural conformation and biological activity of the peptide of the given sequence.

The invention further provides a method for stimulating the in vitro release of prolactin and growth hormone from anterior pituitary cells by incubating the cells in a cell culture medium containing a peptide of formula (I) or a fragment or analog thereof.

In a still further aspect, this invention provides a method for treating growth related disorders characterized by growth hormone deficiencies by administering an effective amount of a peptide of the formula (I) or a fragment or analog thereof to a subject in need of such treatment.

Similarly, the invention provides a method for treating disorders characterized by prolactin hormone deficiencies by administering an effective amount of a peptide of formula (I) or a fragment or analog thereof to a subject in need of such treatment.

Related to these methods is the treatment of subjects having disorders relating to deficiencies in either or both of growth hormone and prolactin hormone by administering to such subjects an effective amount of the subject peptides in combination with another growth hormone stimulant and/or prolactin stimulant, especially GRF and/or TRH.

The present invention also provides pharmaceutical compositions containing minor amounts of the biologically active peptide, with or without another hormone stimulating compound, and a major amount of a pharmaceutically acceptable liquid or solid carrier.

DETAILED DESCRIPTION OF THE INVENTION AND PREFERRED EMBODIMENTS

The present inventor and others have been involved in research for studying the existence of, and identifying, a major biological thymus-brain connection. This research has lead to the conclusion that the thymosins and the endocrine thymus may play a broader role in the physiology of the body than previously suspected. Thus, it appears that the thymus exerts a general role in controlling the aging of other organ and endocrine systems by controlling immunity, and perhaps other systems, by influencing the functioning of T-cells and by feedback loops to the brain. In fact, a number of thymosin peptides in TF-5 have been discovered to have the ability, alone and/or in combination with, for example, pituitary releasing factors, to stimulate the release of various neuropeptides, such as ACTH, luteinizing hormone releasing factor (LRF), luteinizing hormone (LH), β-endorphin, thyrotropin, growth hormone (GH), and prolactin (PRL). This neuropeptide stimulating ability clearly supports a direct link between the endocrine thymus and neuroendocrine system and raises a number of possibilities regarding the physiology of aging. For example, it is possible that the decreased production of thymic hormones, which occurs before the onset of puberty, may provide a first signal to other endocrine and neuroendocrine systems to begin the process of slowing down.

In view of the previously described evidence that pituitary hormones may be regulated by the thymus gland, it was suspected that the thymus secretes a soluble factor capable of regulating pituitary gland function Examination of the effects of the partially purified bovine thymic extract, thymosin fraction 5 (TF-5), upon pituitary hormone release in vitro established that this thymic preparation exhibits potent hormonal-like activities in a variety of lymphocyte assays. Thus, as reported by Spangelo, et al., *Endocrinology*, Vol. 121, No. 6, pages 2035-2043 (1987), TF-5 stimulates the release of GH and PRL, but not LH, from normal anterior pituitary cells in vitro. It is also shown that TF-5 stimulated the release of PRL and GH in the presence of TRH and GRF, respectively, the major known releasing factors for the PRL and GH hormones.

The specific peptide in TF-5 responsible for this activity has now been isolated, identified, and synthetically produced.

MB-35 was first isolated from TF-5 by high performance liquid chromatography (HPLC) using preparative and analytical reverse-phase ($C_{18}$ Delta-Pak) chromatographic columns. The detailed procedure is described in Example 1 to follow.

MB-35 has also been produced using synthetic solid phase peptide synthesis, as shown in Example 3, to follow. The synthetic peptide was purified to substantial homogeneity by HPLC (see FIG. 11). Amino acid analysis and sequencing confirmed the synthetic peptide to be the same substance as the substance MB-35 isolated from TF-5. The synthetic peptide has the same biological activity as the TF-5 derived substance MB-35.

Computer analysis of the sequence of MB-35 using the Protein Identification Resource (PIR) computer system has established that MB-35 is identical to the residues 86-120 of a nuclear protein histone H2A isolated from human, chicken, rat and bovine thymus. Mammalian histone H2A is 129 residues long. Histone H2A is the component of the nuclear protein A24 complex which has been found in several mammalian tissues, including rat liver and calf thymus. Protein A24 is a Y-shaped dimer of histone H2A and non-histone chromosomal protein termed ubiquitin. In bovine thymus A24, the two chains are linked by an isopeptide bond between H2A Lys-119 and the carboxyl-terminal Gly-76 in ubiquitin (FIG. 6, Hunt and Dayhoff, 1988 *Biochem. Biophys. Res. Commun.*, 74, 650-655). Histone H2A from bovine has the following amino acid sequence (using the one-letter code):

```
  1 S G R G K Q G G K A R A K A K T R S S R A G L Q F P V G R V
 31 H R L L R K G N Y A E R V G A G A P V Y L A A V L E Y L T A
 61 E I L E L A G N A A R D N K K T R I I P R H L Q L A I R N D
 91 E E L N K L L G K V T I A Q G G V L P N I Q A V L L P K K T
121 E S H H K A K G K
```

FIG. 1 is a diagrammatic representation of the structure A24 showing the relationship between ubiquitin and histone H2A and the relative location of MB-35.

The full significance of the relationship between MB-35 and histone H2A has not been fully ascertained.

However, at least one recent literature article by R. Reichhart, et al., "Preparations of Homeostatic Thymus Hormone Consist Predominantly of Histone 2A and 2B and Suggest Additional Histone Functions", *Proc. Nat'l Acad. Sci. U.S.A.*, Vol. 82, pp. 5871–4875, August 1985, suggests that some histones may exhibit hormone-like activity. HTH has been ascribed to have various activities, including acting as a synergist of growth hormone. The primary amino acid structures of HTHα/H2A and HTHβ/H2B were screened for similarities between various TF-5 peptides, including thymosins $\alpha_1$, $\alpha_{11}$, $\beta_4$, $\beta_9$ and thymopoietins. No significant similarities were found.

The mechanism by which MB-35 exhibits its hormone release stimulating activity has not yet been elucidated. However, it is anticipated that various modifications of MB-35, including amino acid additions, deletions and/or substitutions can be made without the desired activity being lost. Therefore, any such modifications are considered to fall within the scope of this invention.

For instance, deletions or additions of arbitrary amino acid sequences can be made at either or both of the N- and C-terminals. Preferably such additions or deletions will be made symmetrically at both the N- and C-terminals. When amino acid additions are made, the amino acid sequences may be arbitrarily selected or, more preferably, amino acid sequences may include amino acid residues 85 and below and/or amino acid residues 121 and above of Histone H2A, at the N- and C-terminals, respectively. When additions are made, they will preferably total less than about 14 amino acids, especially less than 10 amino acids, such as 2, 4, 6 or 8 amino acids, since the synthesis of the amino acids become increasingly more difficult as the total number approaches 50 amino acids. Most preferably, therefore, no additional amino acids will be added to either terminal. However, addition of 1, 2 or 3 amino acids or substitution of one or both terminal amino acids for purposes of facilitating the synthesis, e.g. by providing linking sites, or for introducing modifying groups, or for introducing identifying groups, e.g. radioactively labelled Tyr, for radioimmunoassay etc. is often advantageous so long as the modification will not irrevocably impair the desired biological activity. Also, internal additions (i.e. between two adjacent amino acids in MB-35) may also often be permissible, but when made should be limited to 4, especially to 3 or less, such as 0, 1 or 2. When more than one internal amino acid is added, they may be added consecutively (i.e. between adjacent amino acids) or non-consecutively (i.e. between different pairs of adjacent amino acids).

Conversely, deletions of amino acids, preferably from the N- and C-terminals, which do not cause loss of biological activity may often facilitate synthesis. The number of amino acids deleted is not particularly restricted, so long as part or all of the biological activity is retained. Usually this will be the case where the 3-dimensional configuration of the "active site" is not altered. Suitable additions, deletions or substitutions can be readily determined by the practitioner using an appropriate assay for GH and/or PRL stimulation on anterior pituitary cells, such as the assay described in Example 2, supra, without requiring undue experimentation.

When there are amino acids deleted from the peptide MB-35, it is preferred that the deletions be taken from consecutive amino acids at the N- and/or C-terminals. When deletions are taken from both the N- and C-terminals, the deletions are preferably taken symmetrically or nearly symmetrically from each of the N-terminal and C-terminal. Where there are internal deletions these should be preferably limited to 4, especially less than 3, such as 0, 1 or 2, and when there are multiple internal deletions they may be from adjacent amino acids or from non-adjacent amino acids.

Although not intending to be limited thereby, the types of "preserving" substitutions which would be expected to be interchangeable with each other while maintaining the biological activity include, for example, substitutions among the non-polar aliphatic neutral amino acids, including glycine (Gly, G), alanine (Ala, A), proline (Pro, P), valine (Val, V), isoleucine (Ile, I) and leucine (Leu, L); substitutions among the polar aliphatic neutral amino acids, including serine (Ser, S), threonine (Thr, T), methionine (Met, M), cysteine (Cys, C), asparagine P(Asn, N) and glutamine (Gln, G); substitutions among the charged acidic amino acids, including aspartic acid (Asp, D) and glutamic acid (Glu, E); substitutions among the charged basic amino acids, including lysine (Lys, K) and arginine (Arg, R); and substitutions among the aromatic amino acids, including phenylalanine (Phe, F), histidine (His, H), tryptophan (Trp, W) and tyrosine (Tyr, Y), wherein the three letter groups and single letters in the parentheses represent the conventional 3-letter and single letter codes for the respective amino acids.

More broadly, substitutable or interchangeable amino acids will generally often be found from among the foregoing groups as well, especially, for example, from among the following groups: Asp, Glu and His; Asn, Gln, Lys and Arg; Asp, Glu, Lys and Arg; Phe, His, Tyr, Asp, Glu, Ser and Thr; Lys, Ile, Val, Leu, Pro and Arg; Ser, Thr, Ala, Pro and Val; and Gly, Ala, Pro, Asp and Glu. Furthermore, among the aliphatic neutral non-polar amino acids preferred substitutions include Gly and Ala, and Val, Ile and Leu. Ser and Thr is also a preferred group of interchangeable amino acids.

Amino acid additions or substitutions or deletions at the N- and/or C-terminals, generally of 1 or 2 amino acids, are often especially useful since they may serve a variety of functions, such as a linking group, a modifying group, an identifying group (e.g. for radioimmunoassay, etc.) or the like. Often such substitutions, additions or deletions can simplify the synthesis of the peptide, using any of the conventional liquid or solid phase peptide synthesis techniques which are well known in the art.

Thus, the peptides of this invention can be prepared by conventional processes for synthesizing peptides; more specifically, using processes as described, for example, in Schroder and Lubke, *The Peptides*, Vol. 1 (1986), published by Academic Press, New York, U.S.A., or Izumiya et al., *Synthesis of Peptides*, (1975), published by Maruzen Publishing Co., Ltd., for example, the disclosures of which are incorporated herein by reference. Typical methods include an azide process, a chloride process, an acid anhydride process, a mixed anhydride process, a DCC process, an active ester process (a p-nitrophenyl ester process, an N-hydroxysuccinimide ester process, a cynaomethyl ester process, etc.), a process using a Woodward reagent K, a carbodiimidazole process, an oxidation reduction process, a DCC/additive (HONB, HOBt, HOSu) process, etc. Solid phase synthesis is especially preferred.

For example, in case the preferred solid phase synthesis is adopted, the C-terminal amino acid is bound to an insoluble carrier through its carboxyl group. The insoluble carrier is not particularly limited as long as it has a binding capability to a reactive carboxyl group and is inert to the reagents and reaction conditions of the stepwise condensation-deprotection reactions. Examples of such insoluble carriers include halogenomethyl resins such as chloromethyl resin, particularly chloromethyl-polystyrene-divinylbenzene polymer.

After the amino protective group is removed, an amino group-protected amino acid is bound in sequence in accordance with the desired amino acid sequence through condensation of its reactive amino group and the reactive carboxyl group, in sequence, to synthesize step-by-step. After synthesizing the complete sequence, the peptide is split off from the insoluble carrier to produce the protein, using, for example, HF, HBr, or other cleavage agents.

The fully deprotected polypeptide may then be purified by a sequence of chromatographic steps employing any or all of the following types: ion exchange on a weakly basic resin in the acetate form; gel permeation chromatography, e.g. on Sephadex G-25; hydrophobic adsorption chromatography on underivatized polystyrene-divinylbenzene (for example, Amberlite XAD); silica gel adsorption chromatography; ion exchange chromatography, e.g. on Sephadex G-25, or countercurrent distribution; high performance liquid chromatography (HPLC), especially reverse-phase HPLC on octyl-or octadecylsilyl-silica bonded phase column packing.

Although the synthetic peptides according to this invention can be prepared by the above-described chemical preparations, especially the solid phase peptide synthesis, described above, with high efficiency, it is also within the scope of the invention to produce the novel MB-35 peptide or fragments or analogs thereof, by genetic engineering technology, as is now well known in the art. Thus, using appropriate enzymes and microorganisms (e.g. bacteria, such as E. coli) the DNA sequence encoding the desired polypeptide can be incorporated into the genome of the microorganism, thereby causing the microorganism to express the particular peptide of interest.

Once the particular peptide is obtained and purified, it may be used for stimulating release of GH and/or PRL in vitro or in vivo, preferably in vivo, whenever the need therefor is indicated, such as in cases of pituitary dwarfism, lactation disorders, and the like.

Prolactin was first described as being essential for the initiation of lactation of mammals at parturition. In some species, prolactin has been found to also promote milk secretion. In addition, prolactin also initiates secretion of milk in the hypertrophied mammary gland It has been found that prolactin stimulates the synthesis of milk proteins, such as casein and α-lactalbumin. Furthermore, prolactin acts synergistically with estrogen to promote mammary gland proliferation. For a general review of the effects of prolactin see Bern, H. A. and Nicoll, C. S., *Recent Prog. Horm. Res.,* 24, 681 (1968). For a review on the effects of prolactin in human, see Frantz, A. G., et al., *Rec. Prog. Horm. Res.,* 28, 527 (1972).

Prolactin also exhibits an anti-gonadotropic hormone action, that is, prolactin inhibits luteinization by luteinizing hormone and inhibits ovulation induced by pregnant mare's serum. Prolactin induces the secretion of progesterone by the newly formed corpus luteum after ovulation. Progesterone itself inhibits ovulation and it has been noted that the antiovulatory action of prolactin depends on the presence of the corpus luteum. It thus appears that the antiovulatory effect of prolactin may be the result of the prolactin-induced progesterone synthesis by the corpus luteum. For a review of prolactin and human reproduction, see Robyn, C., et al., in *Human Prolactin,* Ed. Pasteels, J. L. and Robyn, C., Americal Elsevier Publishing Co., Inc., New York, p. 167 (1973).

In vitro, prolactin has been found to stimulate glucose uptake and lipogenesis in adipose tissue. When injected, prolactin has been found to mimic a number of actions of growth hormone.

Uses of the peptides of this invention can, therefore, be based on the known biological activities of prolactin as discussed above. For example, MB-35 or its biologically active analogs can be administered to insure adequate milk production for breast-feeding mothers, or to increase the production of milk in dairy cows. The antiovulatory effect of prolactin can be exploited as a birth control measure by using MB-35 or its biologically active analogs alone or in combination with TRH as a female contraceptive.

MB-35 and its biologically active analogs also exhibit growth hormone releasing activity and, based on the known biological activities of growth hormone, the peptides of this invention should be useful in the treatment of growth-related disorders, such as hypopituitary dwarfism and diabetes resulting from abnormalities in growth hormone production. Furthermore, they can also be used to stimulate the growth or enhance feed efficiency of animals raised for meat production, to enhance milk production and stimulate egg production.

Other applications for human treatment include diffuse gastric bleeding, pseudoarthrosis, burn therapy, wound healing, bone knitting, post menopausal osteoporosis, ovarian dysgenesis, and similar disorders associated with deficiencies in GH and/or PRL levels.

The peptides of the invention may be administered alone or in combination with other hormone production stimulating chemicals.

In one particularly preferred embodiment of the invention, the hormone releasing peptide of this invention is used in combination with any of the forms of growth hormone releasing factor, including GRF (1-44), GRF (1-40), GRF (1-37), or the analogs thereof, such as GRF (1-29), GRF (1-32), and the like, in either the amidated ($NH_2$) or free acid (OH) forms of the carboxyl terminus, and/or with thyrotropin releasing hormone (TRH), preferably in ratios which will provide synergistic action of the different pituitary hormone promoting agents.

Pharmaceutical compositions in accordance with the invention include the peptide MB-35 of formula (I) or an analog thereof having from 20 to 50 amino acids in length, preferably 30 to 45 amino acids in length, or a non-toxic salt of any of these, dispersed in a pharmaceutically or veterinarily acceptable liquid or solid carrier.

Appropriate dosages of the peptides of the invention to be administered will vary somewhat depending on the individual subject and the condition being treated. The skilled worker will be able to determine appropriate dosages based on the known circulating levels of growth hormone and prolactin hormone associated with normal physiology and the growth hormone and prolactin hormone releasing activity of the peptide.

Compounds of this invention induce release of prolactin hormone and growth hormone in vitro on the same order of magnitude as that of TRH and GRF. Thus, these peptides can be administered in about the same dosages as if thyrotropin releasing hormone or growth hormone releasing factor alone were given for the same purpose. As is well known in the art treatment of pituitary hormone-related disorders will necessitate varying dosages from individual to individual depending upon the degree of insufficiency of pituitary hormone production. Generally, a dosage range of from 0.04 µg/kg/day to 1 mg/kg/day, preferably from 0.1 µg/kg/day to 0.1 mg/kg/day, such as about 1.0 µg/kg/day based on body weight of the subject may be used to stimulate release of the desired hormone The dosages employed to stimulate growth activity in livestock will be significantly higher (per kg. of subject weight) than the dosages employed to restore normal growth in case of growth hormone deficiencies, such as pituitary dwarfism in humans. In livestock, generally a dosage in the range of from 0.4 µg/kg/day to about 10 mg/kg/day subcutaneously may be used to stimulate release of the desired pituitary hormone.

The present invention also includes within its scope pharmaceutical compositions comprising, as an active ingredient, at least one of the peptides of Formula I in association with a pharmaceutically or veterinarily acceptable liquid or solid carrier or diluent. Optionally, the active ingredient of the pharmaceutical compositions can comprise a growth hormone and/or prolactin hormone promoting agent in addition to at least one of the peptides of Formula I or another composition which exhibits a different activity, e.g. an antibiotic or other pharmaceutically or veterinarily active material.

Growth promoting agents include, but are not limited to, GRF, TRH, diethylstilbestrol, theophylline, enkephalins, E series prostaglandins, compounds disclosed in U.S. Pat. No. 3,239,345, e.g. zeranol, and compounds disclosed in U.S. Pat. No. 4,036,979, e.g. sulbenox.

The peptides of this invention can be administered by oral, parenteral (e.g. intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules In such solid dosage forms, the active compound is admixed with at least one inert pharmaceutically acceptable carrier, such as sucrose, lactose, or starch. Such dosage forms can also comprise, as is normal practice, additional substances other than inert diluents, e.g. lubricating agents, such as magnesium stearate In the case of capsules, tablets and pills, the dosage forms may also comprise buffering agents Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or nonaqueous solutions, suspensions, or emulsions. Examples of nonaqueous solvents or vehicles are propylene glycol, polyethylene glycol, vegetable oils, such as olive oil and corn oil, gelatin, and injectable organic esters, such as ethyl oleate. Such dosage forms may also contain adjuvants, such as preserving, wetting, emulsifying and dispersing agents. They may be sterilized by, for example, filtration through a bacteria-retaining filler, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions of rectal or vaginal administration are preferably suppositories which may contain, in addition to the active substance, excipients, such as cocoa butter or a suppository wax.

Compositions for nasal or sublingual administration are also prepared with standard excipients well known in the art.

When the compounds of this invention are used in combination with another GH and/or PRL promoting agent, such as GRF and TRH, they may be used in any suitable ratio, by weight, for example, from about 100:1 to 1:100, preferably from about 10:1 to 1:10, the preferred ratios being such that the combination synergistically releases the desired pituitary hormone from the pituitary.

The invention will now be described in greater detail by way of the following exemplatory, non-limiting examples.

EXAMPLE 1.

Isolation of MB-35 from TF-5

Figure 2:
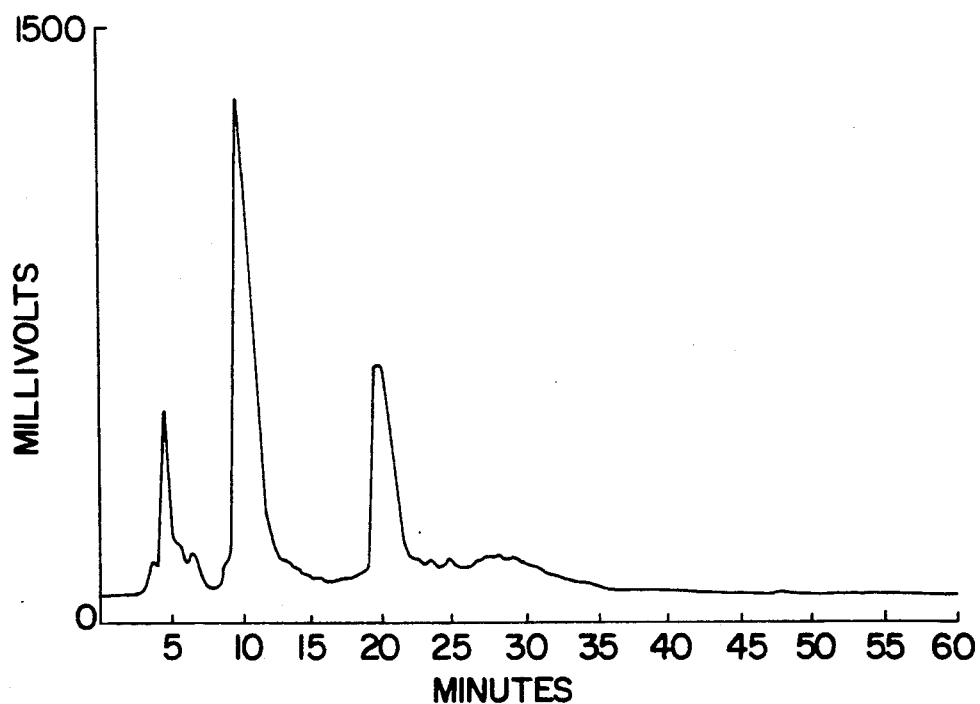
FIG. 2 is a chromatogram from the reverse-phase high pressure liquid chromatographic (RP-HPLC) separation of thymosin fraction 5 (TF-5) on a 300×50 mm Delta-pak column.
Figure 3:
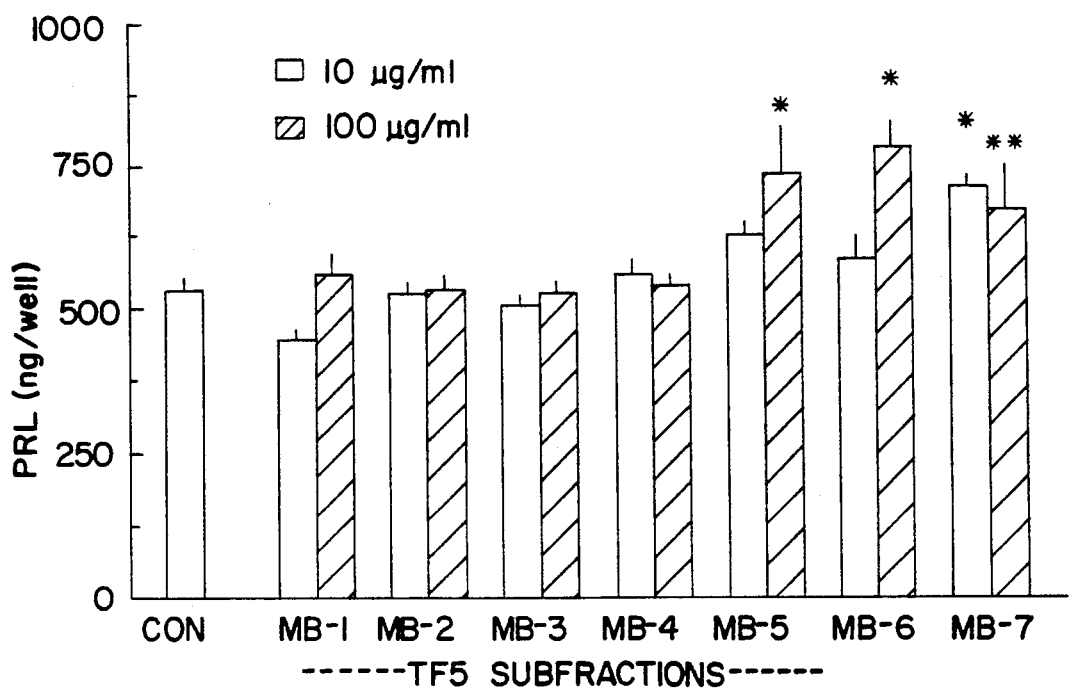
FIG. 3 is a bar graph showing the effect of pooled fractions MB-1 to MB-7 from the RP-HPLC of FIG. 2 in an in vitro assay for prolactin hormone (PRL) release from normal anterior pituitary cells, relative to a control (CON) using only RPMI-1640.
Figure 4:
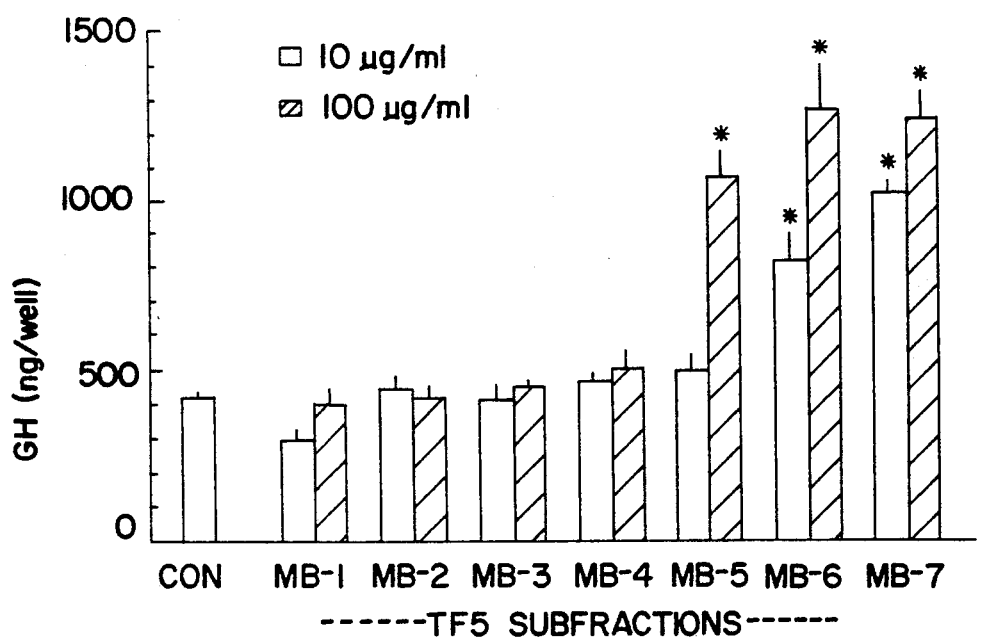
FIG. 4 is a bar chart showing the effect of pooled fractions MB-1 to MB-7 in the in vitro assay for growth hormone (GH) release from normal anterior pituitary cells versus a control.

Preparative reverse-phase chromatography of TF-5 (1.5 g) was performed on a Delta-prep HPLC system equipped with a Model 481 variable-wavelength detector with a semi-preparative flow-cell, set at 280 nm, and a 300×50-mm Delta-pak, 300 ° Å, 15 µm $C_{18}$ column (*Waters). Eluent A was 0.02M ammonium acetate (pH 6.8), and eluent B was acetonitrile. A 60-minute linear gradient from 0–80% B was run at a flow-rate of 80 ml/min. TF-5 was dissolved in the initial buffer and applied to the column through a port in the solvent delivery system. The results are shown in FIG. 2. One-minute fractions were collected and combined into seven different pools called MB-1 to MB-7 in order of increasing hydrophobicity. Normal anterior pituitary cells were treated with each of the seven pools, labelled MB-1, MB-2, MB-3, MB-4, MB-5, MB-6 and MB-7 respectively, at dosages of 10 µg/ml and 100 µg/ml by the PRL and GH assay described below in Example 2. The results are shown in Table 1 and are plotted in FIGS. 3 and 4. HPLC subfractions MB-1G, MB-2G, MB-3G and MB-4G had no significant effect on hormone release as compared to the background (control). In contrast, significant increases ($p<0.01$) in PRL and GH release were observed for MB-5G, MB-6G and MB-7G treated wells. The results are expressed as the mean ±SEM of four wells. MB-7 appeared more potent for stimulation of PRL and GH release because 10 µg/ml of this pool causes a significant increase in these hormones ($p<0.01$), whereas the same amount of MB-5 and TF-5 had no effect for GH release. MB-7 and MB-6, however, do appear to be equipotent for stimulating PRL and GH release, using 100 µg/ml, but MB-7 appeared more potent using 10 µg/ml. Only 100 µg/ml TF-5 significantly stimulated hormone release.

TABLE 1

Effect of HPLC fractions of TF-5 on Prolactin and Growth Hormone release from anterior pituitary cells in vitro.

| HPLC Fraction | GH (ng/ml) | | PRL (ng/ml) | |
|---|---|---|---|---|
| Tested | 100 μg/ml | 10 μg/ml | 100 μg/ml | 10 μg/ml |
| MB-1 | 404 ± 43.1 | 310 ± 29.1 | 562 ± 32.0 | 447 ± 14.5 |
| MB-2 | 425 ± 32.8 | 450 ± 28.6 | 534 ± 25.9 | 529 ± 17.2 |
| MB-3 | 454 ± 15.0 | 419 ± 39.5 | 531 ± 17.4 | 507 ± 13.3 |
| MB-4 | 505 ± 47.0 | 470 ± 20.7 | 546 ± 17.1 | 563 ± 25.5 |
| MB-5 | 1075 ± 68.8* | 498 ± 42.9 | 738 ± 78.9* | 631 ± 15.6 |
| MB-6 | 1271 ± 122* | 818 ± 74.2* | 787 ± 42.0* | 591 ± 29.1 |
| MB-7 | 1248 ± 70.4* | 1025 ± 34.2* | 675 ± 76.8** | 716 ± 16.3* |
| Medium Control | | 423 ± 12.2 | | 533 ± 19.4 |

*p < 0.01 vs. Control
**p < 0.05 vs. Control

Further analysis of the individual fractions 41-57 (F-41 to F-57) in pool MB-7 indicated that the peptide with hormone-releasing activity elutes in Fraction 46 (F-46), the peak of activity. Therefore, F-46 was used for further purification.

Figure 5:
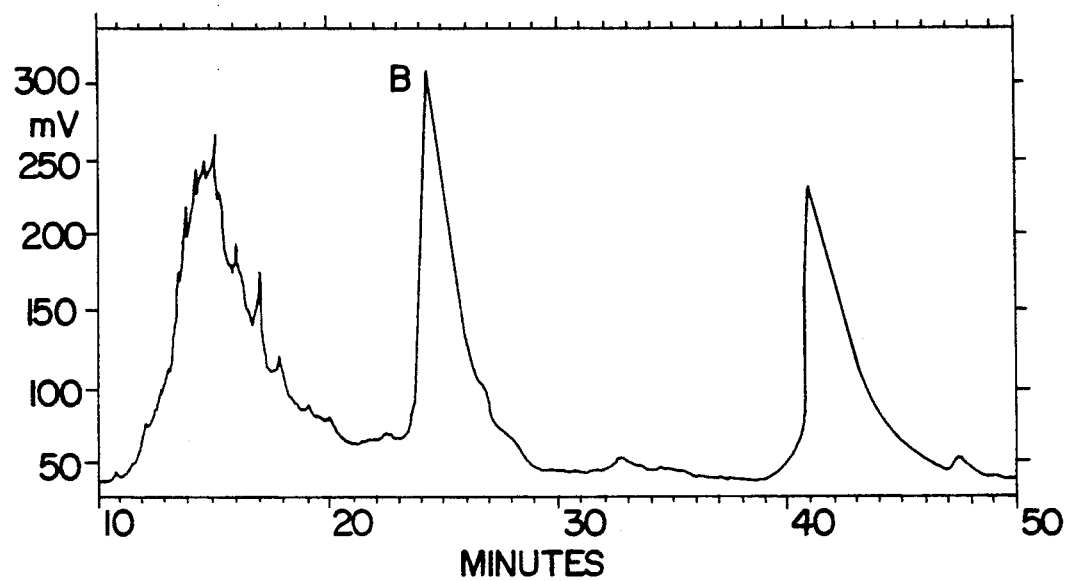
FIG. 5 is a chromatogram obtained from the rechromatography of fraction 46 (F-46) from pool MB-7 of the RP-HPLC-chromatogram of FIG. 2 on a 150×3.9 mm I.D. Delta-pak column.
Figure 6:
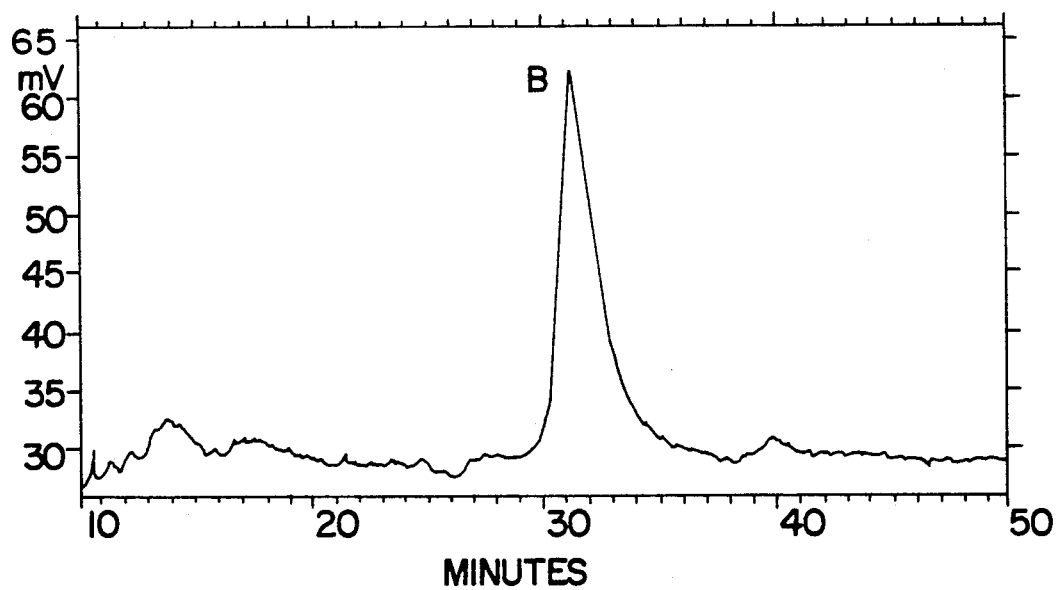
FIG. 6 is a chromatograph obtained from the rechromatography of fraction 49 (F-49) from the RP-HPLC chromatogram of F-46 in FIG. 5.

F-46 was, therefore, further fractionated on a 150×3.9 mm-I.D. Delta-pak 300 Å 5 μm $C_{18}$ column using model 510 HPLC system (Waters), equipped with Model 441 detector set at 214 nm. Eluent A was 0.1% trifluoroacetic acid (TFA) in water and eluent B was acetonitrile with 0.1% TFA. Separation was achieved with 10- minute linear gradient from 0–29% B, followed by a 25-minute hold at 29% B. At 35.1-minute gradient was increased to 30% B followed by a 20-minute hold at 30% B. At 55.1-minute the column was washed with 50% B for 10 minutes. The results of the RP-HPLC of F-46 is shown in FIG. 5. One half minute fractions were collected and assayed for hormone-releasing activity using normal anterior pituitary cells, as described below. Results indicated that the peptide with hormone releasing activity elutes in Fraction 49 (F-49), the peak of activity. F-49 (Peak B) in FIG. 5 was concentrated to 300 μl to remove acetonitrile and rechromatographed under the same conditions The results are shown in FIG. 6. The peak (identified as Peak B in FIG. 6) was collected and identified as peptide MB-35 and subjected to isoelectric focusing (IEF), SDS-PAGE, amino acid composition and sequence analysis The yield of peptide MB-35 from TF-5 is about 0.1%. The preparation was free of impurities as evidenced by HPLC and IEF and SDS-PAGE analysis.

The following table shows the specific activity (nanogram hormone produced per microgram of peptide) as a function of the different purification steps from TF-5 to MB-35:

| Purification Step (Active Fraction) | Specific Activity (ng/μg peptide) | |
|---|---|---|
| | PRL | GH |
| TF-5 | 5 | 10 |
| MB-7 | 2 | 8 |
| F-46 | 6.4 | 21 |
| MB-35 | 226 | 98 |

Data from all the chromatographic procedures was collected using a Model 840 chromatography work station (Waters).

Figure 7:
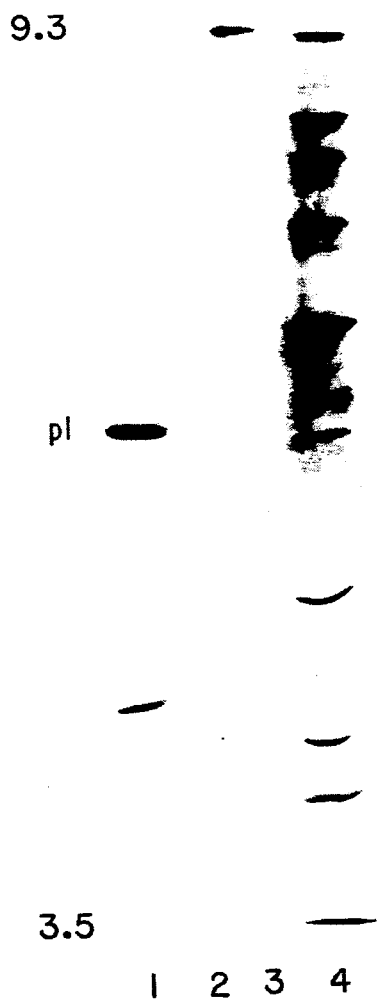
FIG. 7 is a photograph of IEF focussing on the peptide MB-35 according to this invention (Lane 1), thymosin fraction 5 (Lane 2), Histone 2A (Lane 3) and LKB/Pharmacia IEF pH markers, pH 3-10 (Lane 4)

Isoelectric focusing was conducted for 90 minutes using an LKB Pharmacia isoelectric focusing gel, pH 3.5–9.5 at a constant power of 25 watts (LKB Model 2103 power supply). The gels were fixed in 20% trichloroacetic acid and 3.5% sulfosalicylic acid for one hour. They were stained in 0.1% Coomassie Blue R 250 in staining solution and destained in acetic acid, ethanol and water (1:3.8, V/V). Proteins were also visualized by silver staining with the Bio-Rad silver-stain kit. The results are shown in FIG. 7 for IEF on MB-35 (200 μg) in Lane 1, TF-5 (75 μg) in Lane 2, Histone 2A (10 μg) in Lane 3 and LKB/Pharmacia IEF pH markers, pH 3-10 (10 μg) in Lane 4.

Figure 14:
FIG. 14 is a photograph of SDS-PAGE on peptide MB-35 (Lane 2) and low molecular weight markers from BioRad (Lane 1).

SDS-PAGE was performed using a 1.5 mm 16% SDS-Polyacrylamide gel according to the method of Laemmli (1970) and stained using Coomassie Blue. The results are shown in FIG. 14 wherein Lane 1 shows the bands for low molecular weight markers (1 μl ) from BioRad and Lane 2 shows the band for MB-35 (2 μl ) appearing at molecular weight 3756.

Amino acid analysis was performed with the Pico-Tag amino acid analysis system of Waters-Millipore. The method is based on the formation of a phenylthiocarbamyl (PTC) derivative of the amino acids from acid-hydrolyzed proteins. Peptide MB-35 samples (about 1–5 μg) were hydrolyzed in 200 ml of a constant boiling HCl atmosphere containing 1% (V/V) phenol, at 110° C. for 24, 48, 72 and 120 hours in the Pico-Tag work station. The hydrolysates were dried and the amino acids were derivatized with phenylisothiocyanate (PITC) for 20 minutes at room temperature to yield the corresponding phenylthiocarbamyl derivatives. These derivatives were analyzed with the Pico-Tag amino acid analysis system, which had been previously calibrated with a standard mixture of amino acids. Table 2 shows the assumed number of residues per molecule based on these analyses. The number of residues based upon sequence analysis is also given in Table 2.

Amino acid sequence analysis was performed on Beckman 890M sequencer using Beckman standard operating program 52285. The sequencer products were identified using Model 510 HPLC system (Waters), equipped with Model 441 detector set at 254 nm. The peptide sequence derivatives, phenylthiohydantoin (PTH) amino acids were reconstituted in 10 μl of acetonitrile and 2 μl was injected to the 150×3.0 mm Nova-Pak $C_{18}$ column. Eluent A was 25 mM na-acetate pH 5.00 in acetonitrile (5.5:1, V/V) and eluent B was 2-propanol in water (3.2, V/V). The column temperature was held at 40° C. The gradient conditions were as follows:

| | | Gradient Table | | |
|---|---|---|---|---|
| Time | Flow | % A | % B | Curve # |
| 0 | 1 | 100 | 0 | |
| 1.0 | 1 | 100 | 0 | 6 |

| Gradient Table | | | | |
|---|---|---|---|---|
| Time | Flow | % A | % B | Curve # |
| 7.5 | 1 | 60 | 40 | 4 |
| 9.0 | 1 | 60 | 40 | 6 |
| 9.5 | 1 | 100 | 0 | 6 |

TABLE 2

Amino Acid Composition of Peptide MB-35

| Amino Acid | Number of residues from acid hydrolysis* | Number of residues from the sequence |
|---|---|---|
| D | 4.0+ | 1 |
| E | 4.0+ | 2 |
| S | 0.4 | 0 |
| G | 3.4 | 3 |
| H | 0.2 | 0 |
| R | 1.0 | 1 |
| T | 1.5 | 2 |
| A | 3.4 | 3 |
| P | 1.9 | 2 |
| Y | 0.0 | 0 |
| V | 2.6 | 3 |
| M | 0.0 | 0 |
| C | 0.0 | 0 |

Ala—Ile—Arg—Asn—Asp—Glu—Glu—Leu—Asn—Lys—Leu—Leu—Gly—Lys—Val—Thr—Ile—Ala—Gln—Gly—Gly—Val—Leu—Pro—Asn—Ile—Gln—Ala—Val—Leu—Leu—Pro—Lys—Lys—Thr

| | | |
|---|---|---|
| I | 2.5 | 3 |
| L | 5.5 | 6 |
| F | 0.0 | 0 |
| K | 4.4 | 4 |
| N | — | 3 |
| Q | — | 2 |

Footnotes Table 2:
*The data are presented as numbers of residues per molecule.
+ Aspartic acid and glutamic acid values are the sum of their acids and amides.

EXAMPLE 2

PRL and GH Assay

Anterior pituitary cells from normal adult female or male Sprague-Dawley rats were dispersed as described by Cronin and Thorner (Cronin, M. M., and Thorner, M. O., 1982 *J. Cyclic Nucleotide Res.*, 8, 267). Normal cells were seeded onto 24-well plates (Falcon, Oxnard, Calif.) at a density of $0.5 \times 10^6$ viable cells/well into complete medium (RPMI-1640 containing 2.5% fetal calf serum (FCS), 7.5% horse serum, 100 μg/ml Penicillin G, and 3.8 μg/ml fungizone (Gibco, Grand Island, N.Y.)). The cells were allowed to attach to the wells in a humidified atmosphere of 5% $CO_2$ - 95% air at 37° C. for a minimum period of four days before an experiment was performed. On the day of an assay, the cells were rinsed twice (1 hour each) with serum-free RPMI-1640 medium containing antibiotics. Inhibitory neurohormones and drugs were added during the final 20 minutes of the second rinse. Test substances were placed in the wells at varying concentrations (dilutions) and incubated in a humidified atmosphere of 5% $CO_2$ - 95% air at 37° C. for a period of 30 minutes. After incubations, the medium is quickly removed and saved for radioimmunoassay (RIA).

PRL and GH were determined by standard RIA techniques (media diluted 1:30, 25–70 μl samples) using materials and protocols supplied by the NIDDK Rat Pituitary Hormone Distribution Program. Inter- and intra-assay variations for PRL and GH were less than 8% to 10%, respectively. All samples were assayed in duplicate, with results expressed in terms of NIDDK standards (rat PRL RP-2 and rat GH RP-1). TF-5 did not have PRL and GH cross-reactive material in the concentrations used.

Figure 8:
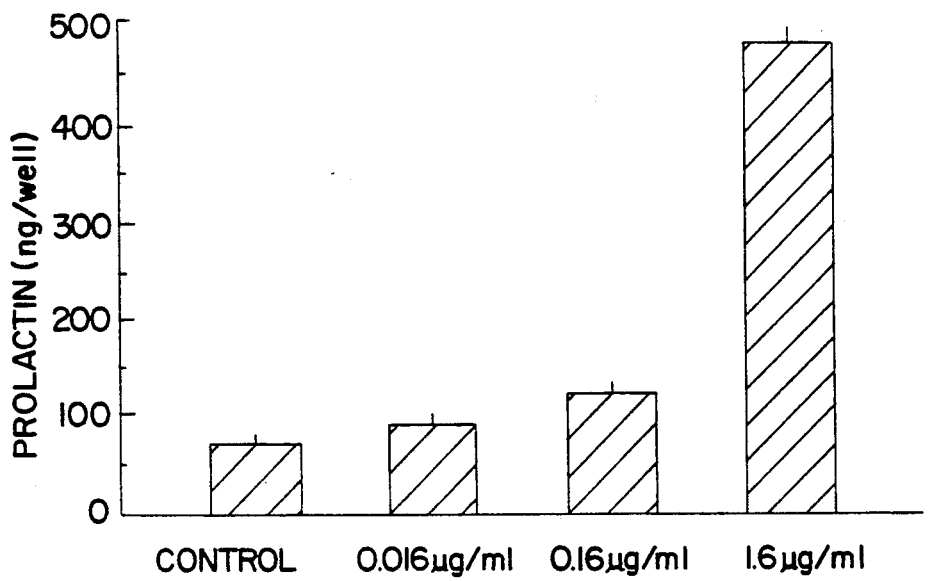
FIG. 8 is a bar graph showing the effect of different concentrations of MB-35 in the in vitro assay for PRL production.

Treatment of normal anterior pituitary cells with different doses (0.06, 0.16 and 1.6 μg/ml) of peptide result in a significant (p<0.01) increase in PRL and GH release at the 0.16 μg/ml dosage. The results are shown in FIG. 8.

Figure 9:
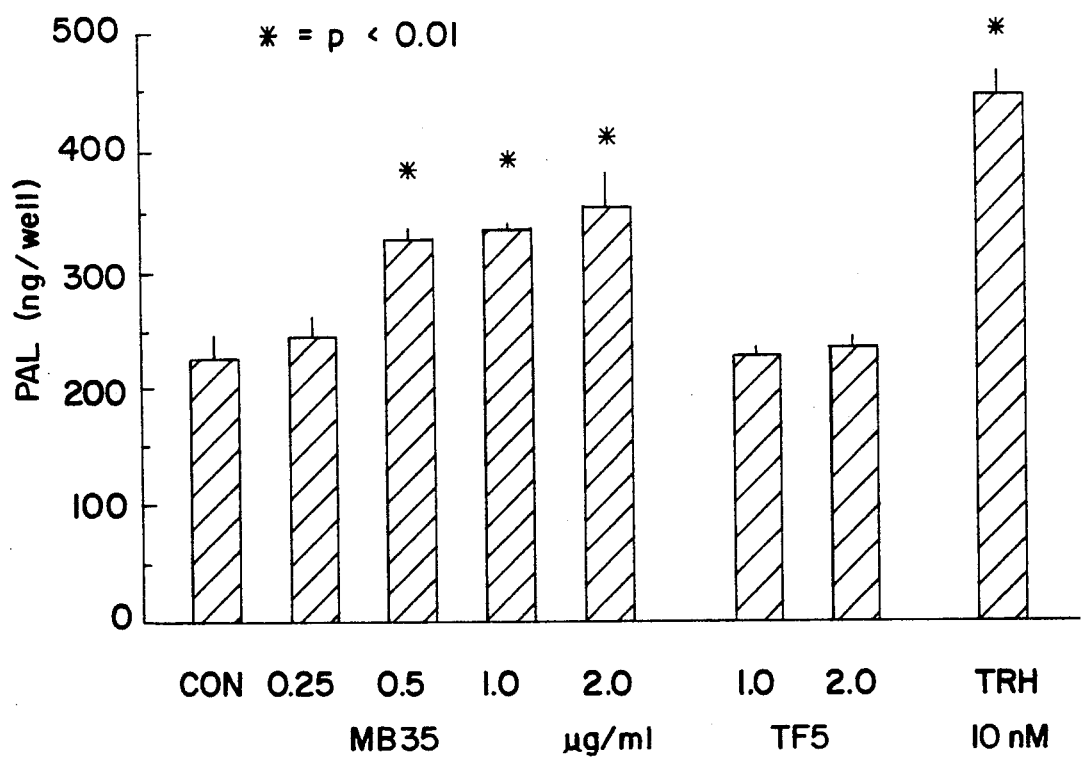
FIG. 9 is a bar graph showing the effect of different concentrations of MB-35, TF-5 and TRH in the in vitro assay for PRL production.

In a second series of concentration-dependant tests for measuring the influence of the purified peptide MB-35 on PRL and GH release from anterior pituitary cells, in vitro, the MB-35 concentrations were tested at 0.25, 0.5, 1.0 and 2.0 μg/ml. As a control, the cells were incubated with RPMI-1640 medium without peptide (the same is true for all other assays). Also tested in this assay were TF-5 at 1.0 and 2.0 μg/ml and TRH at 10 nM. The results are shown in FIG. 9 (expressed as the mean ±SEM of four wells). Peptide MB-35 is significantly more potent than the partially purified thymosin fraction 5 (TF-5) in stimulating PRL and GH release.

EXAMPLE 3

Chemical synthesis of Peptide MB-35

A. Boc-Thr(Bzl)-$OCH_2$-$C_6H_4$-Resin (1.0 g; 0.5 mmol) was placed in a 150 mL peptide synthesis flask and the following steps of the operation were performed in each solid phase peptide synthesis cycle (20 volumes of solvent or reagent was used in each step unless otherwise stated):

(1). prewash with 50% TFA in methylene chloride;
(2). stir 30 minutes in 50% TFA in methylene chloride;
(3). wash 3 times with methylene chloride;
(4). prewash with 10% triethylamine in methylene chloride;
(5). stir 3 minutes in 10% triethylamine in methylene chloride;
(6). test for ninhydrin reaction (should be very strongly positive at this step; if not, abort the entire synthesis);
(7). add Boc-Lys(ClZ)-OH (0.62 g; 1.5 mmol) and DCC (0.31 g; 1.5 mmol) in 12 volumes of methylene chloride, then stir for 30 minutes;
(8). wash 2 times with 50% isopropyl alcohol in methylene chloride;
(9). wash 3 times with methylene chloride;
(10). test for ninhydrin reaction (should be negative at this point; if not, repeat steps 7–10 until the test becomes negative).

The synthetic cycle was repeated using the following amino acids (each 1.5 mmol), sequentially, one at a time, in step number 7:

Boc—Lys(ClZ)—OH, Boc—Pro—OH, Boc—Leu—OH,
Boc—Leu—OH, Boc—Val—OH, Boc—Ala—OH, Boc—Gln—OH,
Boc—Ile—OH, Boc—Asn—OH, Boc—Pro—OH, Boc—Leu—OH,
Boc—Val—OH, Boc—Gly—OH, Boc—Gly—OH, Boc—Gln—OH,
Boc—Ala—OH, Boc—Ile—OH, Boc—Thr(Bzl)—OH,
Boc—Val—OH, Boc—Lys(ClZ)—OH, Boc—Gly—OH,
Boc—Leu—OH, Boc—Leu—OH, Boc—Lys(ClZ)—OH,
Boc—Asn—OH, Boc—Leu—OH, Boc—Glu(OBzl)—OH,
Boc—Glu(OBzl)—OH, Boc—Asp(OBzl)—OH, Boc—Asn—OH,
Boc—Arg(Tos)—OH, Boc—Ile—OH and Boc—Ala—OH.

For any synthetic cycle involving Boc-Gln-OH or Boc-Asn-OH in coupling reaction at step 7, HOBT (0.41 g; 3.0 mmol) was added into the reaction mixture and the reaction allowed to proceed for 180 minutes using DMF as solvent.

On completion of the synthetic cycles, 2.53 g of the protected peptide resin, Boc-Ala-Ile-Arg(Tos)-Asn-Asp(OBzl) -Glu(OBzl)-Glu(OBzl)-Leu-Leu-Gly-Lys(ClZ)-Val-Thr(Bzl) -Ile-Ala-Gln-Gly-Gly-Val-Leu-Pro-Asn-Ile-Gln-Ala-Val-Leu-Leu-Pro -Lys(ClZ)-Lys(ClZ)-Thr(Bzl)-OCH$_2$-C$_6$H$_4$-Resin, was obtained.

Part of this protected peptide resin (1.5 g) was mixed with 3 mL of anisole and treated with approximately 25 mL of anhydrous HF at 0° for 45 minutes. Upon removal of the excess acid ether, a slightly off-white colored powder was obtained. The peptide material was extracted from the powder with 50 mL of 5% acetic acid, concentrated into a smaller volume, desalted on a Sephadex G-10 column (2.6×85 cm, 0.1M HOAc) and lyophilized to give 0.34 g of crude product, MB-35.

B. Purification of synthetic peptide MB-35

Figure 10:
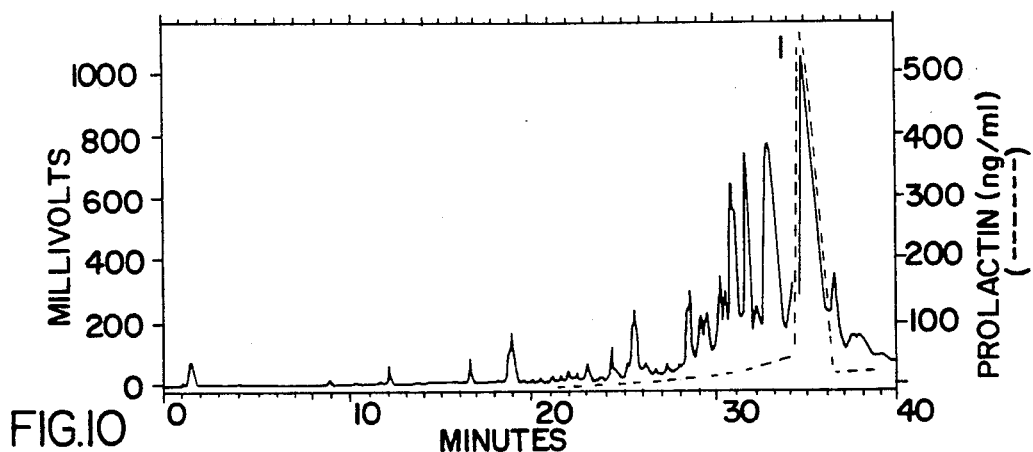
FIG. 10 is a chromatogram of the crude synthetic peptide MB-35 produced as shown in Example 3A from RP-HPLC separation on a 150×3.9 mm I.D. Delta-pak column.
Figure 11:
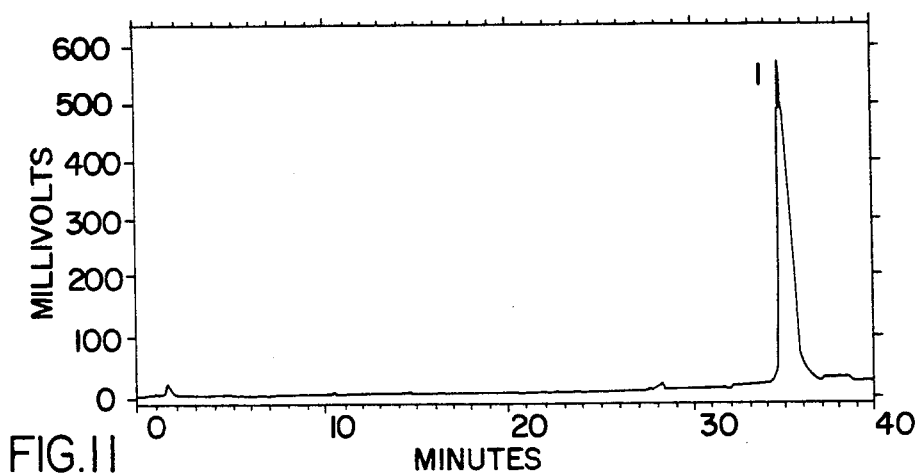
FIG. 11 is a chromatogram obtained from the rechromatography of fraction 36 from the RP-HPLC chromatogram of FIG. 10.

Crude peptide MB-35 from part A above was purified on a 150×3.9 mm-I.D. Delta-pak 300 Å 5 μm C$_{18}$ column using model 510 HPLC system (Waters), equipped with model 441 detector set at 214 nm. Eluent A was 20 mM potassium phosphate buffer, pH 6.0 and Eluent B was acetonitrile with 50% Eluent A. Separation of synthetic peptide MB-35 was achieved with a 40-minute linear gradient from 0-40% B. Results indicated that synthetic peptide MB-35 elutes in Fraction 36 (F-36), the peak of activity (FIG. 10). Collected 1 minute fractions were assayed (as described in Example 2) for PRL releasing activity and the results are also shown (as a dotted line) overlaid on the HPLC chromatogram of FIG. 10. F-36 was concentrated to remove acetonitrile and rechromatographed under the same conditions (FIG. 11). The peak was collected and subjected to IEF and amino acid composition analysis (Table 3).

TABLE 3

| | Amino Acid Composition of Peptide MB-35 | |
|---|---|---|
| Amino Acid | Number of residues from acid hydrolysis* | Number of residues from the sequence |
| D | 3.9+ | 1 |
| E | 3.8+ | 2 |
| G | 3.0 | 3 |
| R | 0.9 | 1 |
| T | 1.7 | 2 |
| A | 2.9 | 3 |
| P | 1.5 | 2 |
| V | 2.8 | 3 |
| I | 3.1 | 3 |
| L | 6.2 | 6 |
| K | 4.1 | 4 |
| N | —* | 3 |
| Q | —* | 2 |

*The data are presented as numbers of residues per molecule.
+ Aspartic acid and glutamic acid values are the sum of their acids and amides.

EXAMPLE 4

This example demonstrates the effect of MB-35 on TRH- and GRF-stimulated hormone release.

Using the PRL and GH assays described above, anterior pituitary cells are coincubated with 10 or 100 μg/ml MB-35 and 100 nM TRH or 10 nM GRF and also with only RPMI medium as control.

Figure 12:
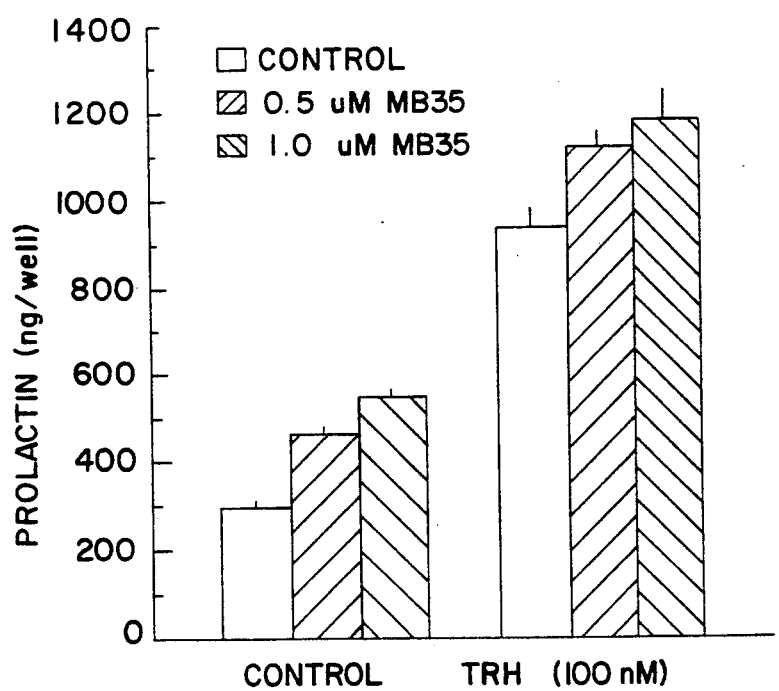
FIG. 12 is a bar graph showing the effect of combinations of MB-35 and TRH in the in vitro assay for PRL productions.

The results are shown in FIGS. 12 and 13.

Incubation of anterior pituitary cells with MB-35 elicited a concentration-related stimulation of PRL release (p<0.01, FIG. 12), with a maximum stimulatory concentration of TRH resulting in a 480% increase in this release compared to the control value. Coincubation of 10 or 100 μg/ml MB-35 with 100 nM TRH produced an additive increase in PRL release. Since MB-35 increases TRH-induced PRL release by the same increment as it increases basal PRL release, and further, since MB-35 stimulation of PRL release is not apparently mediated through increased hydrolysis of polyphosphoinositide (as is the case with TRH stimulation, see Spangelo, et al. at p. 2041), it can be concluded that MB-35 exerts its action on the pituitary cells by a mechanism different from that of TRH.

Similarly, treatment with MB-35 and GRF results in an additive increase in GH release (FIG. 13), again suggesting that MB-35 and GRF exert their hormone stimulating effects by different mechanisms.

What is claimed is:

1. A peptide having the formula

Ala—Ile—Arg—Asn—Asp—Glu—Glu—Leu—Asn—Lys—

Leu—Leu—Gly—Lys—Val—Thr—Ile—Ala—Gln—Gly—

Gly—Val—Leu—Pro—Asn—Ile—Gln—Ala—Val—Leu—

Leu—Pro—Lys—Lys—Thr.

2. A method for stimulating the in vitro release of prolactin and growth hormone from anterior pituitary cells which comprises incubating the cells in a cell culture medium containing a peptide having the composition as set forth in claim 1.